(12) United States Patent
Knoblach

(10) Patent No.: US 10,126,212 B2
(45) Date of Patent: Nov. 13, 2018

(54) HOSE OR TUBE FOR TRANSPORTING A GAS SPECIMEN

(71) Applicant: AREVA GMBH, Erlangen (DE)

(72) Inventor: Walter Knoblach, Forchheim (DE)

(73) Assignee: AREVA GmbH, Erlangen (DE)

(*) Notice: Subject to any disclaimer, the term of this patent is extended or adjusted under 35 U.S.C. 154(b) by 5 days.

(21) Appl. No.: 15/134,414

(22) Filed: Apr. 21, 2016

(65) Prior Publication Data

US 2016/0231204 A1    Aug. 11, 2016

Related U.S. Application Data

(63) Continuation of application No. PCT/EP2014/073096, filed on Oct. 28, 2014.

(30) Foreign Application Priority Data

Oct. 28, 2013  (DE) .................. 10 2013 221 799

(51) Int. Cl.
| | | |
|---|---|---|
| *F17D 5/02* | (2006.01) | |
| *G01N 1/22* | (2006.01) | |
| *G01M 3/22* | (2006.01) | |
| *G01N 1/10* | (2006.01) | |
| *G01N 1/26* | (2006.01) | |

(52) U.S. Cl.
CPC ............. *G01N 1/22* (2013.01); *F17D 5/02* (2013.01); *G01M 3/22* (2013.01); *G01N 1/10* (2013.01); *G01N 1/2273* (2013.01); *G01N 1/26* (2013.01); *G01N 2001/2285* (2013.01)

(58) Field of Classification Search
CPC ....................................................... G01N 1/22
USPC .................. 138/104, 114, 137, 140, 148
See application file for complete search history.

(56) References Cited

U.S. PATENT DOCUMENTS

| | | | |
|---|---|---|---|
| 3,977,233 A | 8/1976 | Issel | |
| 4,735,095 A | 4/1988 | Issel | |
| 5,010,776 A * | 4/1991 | Lucero ............. | B09B 1/00 |
| | | | 73/863.23 |
| 5,589,647 A | 12/1996 | Jax et al. | |
| 6,180,909 B1 * | 1/2001 | Quick ............. | B01D 29/111 |
| | | | 219/85.13 |

(Continued)

FOREIGN PATENT DOCUMENTS

| | | | | |
|---|---|---|---|---|
| CA | 2665814 A1 * | 8/2008 | ............. | F17D 5/02 |
| CN | 1492802 A | 4/2004 | | |

(Continued)

*Primary Examiner* — Craig Schneider
*Assistant Examiner* — David Deal
(74) *Attorney, Agent, or Firm* — Laurence A. Greenberg; Werner H. Stemer; Ralph E. Locher

(57) ABSTRACT

A hose or tube for transporting a gas specimen has an inner envelope, forming a diffusion barrier and containing a plurality of perforation holes, and an outer envelope, forming a diffusion layer and resting on the inner envelope. The object is to develop a hose or tube so as to ensure transport of a gas specimen over as great a distance as possible without substantial weakening of the concentration, and at the same time without impairing the ability of the gas to be detected to diffuse into the hose or tube. For this purpose, the outer envelope contains diffusion-inhibiting sealing zones on its inner surface, which zones overlap the perforation holes in the inner envelope.

12 Claims, 1 Drawing Sheet

(56) References Cited

U.S. PATENT DOCUMENTS

| | | | |
|---|---|---|---|
| 6,685,872 B2 | 2/2004 | Dooley et al. | |
| 7,270,019 B2 | 9/2007 | Issel | |
| 8,875,563 B2 | 11/2014 | Fleischer | |
| 9,103,742 B2 | 8/2015 | Fleischer et al. | |
| 2007/0113912 A1 | 5/2007 | Lawrence | |
| 2008/0053198 A1* | 3/2008 | Issel | F16L 11/12 73/40.5 R |
| 2009/0148348 A1* | 6/2009 | Pettigrew | C08J 7/126 422/400 |
| 2010/0084035 A1* | 4/2010 | Binet | F16L 11/083 138/104 |
| 2010/0224541 A1 | 9/2010 | Takabatake et al. | |

FOREIGN PATENT DOCUMENTS

| | | |
|---|---|---|
| CN | 101270836 A | 9/2008 |
| CN | 101821206 A | 9/2010 |
| DE | 2431907 A1 | 1/1976 |
| DE | 4242806 A1 | 6/1994 |
| DE | 102007042160 B3 | 10/2008 |
| DE | 102008014808 B4 | 1/2012 |
| EP | 0175219 B1 | 5/1988 |
| WO | 2005015070 A1 | 2/2005 |
| WO | 2006122696 A1 | 11/2006 |

\* cited by examiner

HOSE OR TUBE FOR TRANSPORTING A GAS SPECIMEN

CROSS-REFERENCE TO RELATED APPLICATION

This is a continuation application, under 35 U.S.C. § 120, of copending international application No. PCT/EP2014/073096, filed Oct. 28, 2014, which designated the United States; this application also claims the priority, under 35 U.S.C. § 119, of German patent application No. DE 10 2013 221 799.4, filed Oct. 28, 2013; the prior applications are herewith incorporated by reference in their entirety.

BACKGROUND OF THE INVENTION

Field of the Invention

The present invention relates to a hose or tube for transporting a gas specimen, having an inner envelope, forming a diffusion barrier and comprising a plurality of perforation holes, and an outer envelope, forming a diffusion layer and resting on the inner envelope.

A hose of this type, which is also known as a sensor hose, is known for example from European patent EP 0 175 219 B1, corresponding to U.S. Pat. No. 4,735,095. The invention described therein relates to a hollow line for use in determining concentration profiles of liquid or gaseous substances over a distance, the line intended to receive a testing medium to be passed there through at intervals and to be guided past a detector being configured so that the substances can penetrate into the inside of the line. This hollow line consists of a material through which the substances can diffuse into the inside of the line. A hollow inner line is provided inside the line, the wall of which inner pipe has openings and which inner pipe consists of a material impermeable to the substances.

A disadvantage of hoses of this type is that, although the substance to be detected can diffuse into the inside of the hose from outside and can be guided therein by a transport or scavenging gas to a remote detector, a portion of the gas specimen nevertheless escapes again, via the perforation openings in the inner envelope, into the surroundings during transport. Although an appropriate number, size and distribution of the perforation holes can result in a certain optimization in this regard, in practice the achievable transport distances are typically limited to a maximum of 2 km to 5 km. This is in any case true for substances which are difficult to detect, relatively little of which substances diffuse into the hose at the leak site, meaning that the adsorption/diffusion losses along the transport path have particularly significant consequences.

SUMMARY OF THE INVENTION

The object of the invention is to develop a hose or tube of the above-mentioned type so as to ensure transport of a gas specimen over as great a distance as possible without substantial weakening of the concentration, and at the same time without impairing the ability of the gas to be detected to diffuse into the hose or tube.

This object is achieved according to the invention by the fact that the outer envelope contains diffusion-inhibiting or diffusion-preventing sealing zones on its inside or inner surface, which zones overlap the perforation holes in the inner envelope and thus essentially form cover-like local barrier layers.

The invention is based on the finding that, when there is a sufficiently high concentration in the surroundings, gas molecules diffuse into the diffusion layer from the outside and thereby cause the outer envelope to swell. This in turn causes the outer envelope, which usually rests on the inner envelope, to lift off the inner envelope, even in the region of the sealing zones. In this way, the gas molecules can flow through the diffusion layer of the outer envelope, the temporary gap formed between the outer envelope and the inner envelope and through the perforation holes, thus bypassing the sealing zones, almost unimpeded into the inside of the hose or tube. On the other hand, in the portions of the transport path where negligible concentrations of diffusible gases are present in the external surroundings of the hose or tube, the outer envelope fits closely to the inner envelope. The sealing zones overlapping the perforation holes thus plug possible leakage paths to the outside for the gas specimen transported in the inside. As a result, a "diffusion diode" is produced in this way—at least in principle—which permits diffusion from the outside to the inside, but prevents or at least greatly inhibits it in the opposite direction. In practice, however, the gas molecules can actually also pass, to a certain extent, through the respective sealing zone, but in any case in a significantly lower quantity/at a lower diffusion current than without the sealing zone.

For a particularly effective use of this effect, it is advantageous for the sealing zones to overlap substantially all the perforation holes, so that each perforation hole is substantially assigned a sealing zone.

On the other hand, it is preferred for the sealing zones to be arranged substantially exclusively in the region of the perforation holes and not in the region of the spaces between the perforation holes. This ensures that the gas molecules can flow substantially unimpeded between the sealing zones and into the gap between the inner envelope and the outer envelope and finally through the perforation holes into the inside of the tube or hose when the outer envelope is swollen.

To achieve a good compromise between a sufficient sealing effect when the diffusion diode is closed and flow cross sections of sufficient dimensions when the flow diode is open, the overlap is preferably selected such that the ratio of the overlapped marginal surface of the inner envelope to the hole surface of the corresponding perforation hole is in the range of 0% to 50%.

In an advantageous configuration, the corresponding sealing zone is formed by a chemical and/or physical treatment of the surface of the outer envelope in this region, in particular by contact with a fluorine-containing gas.

In a further preferred configuration, the inner envelope of the hose or tube is substantially completely covered on its inside or inner surface by a sealing layer or sealing expediently formed by a chemical and/or physical treatment of the surface of the inner envelope, in particular generated through contact with a fluorine-containing gas. A sealing of this type on the inner surface defining the flow channel increases the diffusion-resistance of the inner envelope and in particular reduces the adsorption of gas molecules at the inner surface.

In the case of fluorination or the application of another process gas in order to achieve a similar effect, it is preferably possible to produce a hose or tube of the type according to the invention, in that a hose or a tube having an inner envelope, forming a diffusion barrier and containing a plurality of perforation holes, and an outer envelope, forming a diffusion layer and resting on the inner envelope, is provided. A process gas, in particular containing fluorine as the reactive component and for example containing nitrogen as the carrier gas, is applied to the hose or tube from the inside for an appropriate treatment time. A typical configuration is, for example, 10% $F_2$ in 90% $N_2$, <200 mbar overpressure compared with the surrounding atmospheric pressure, room temperature, >8 hours exposure time. Thus, as a result of irreversible chemical surface reactions, when the outer envelope has suitable properties, the desired sealing zones are formed in the region of the allocated perforation holes. Depending on the properties of the inner envelope, this envelope is sealed at the same time by similar surface reactions. When the inner envelope is made of materials for which these reaction mechanisms are not available, the sealing regions are formed at least on the outer envelope.

In order to allow particularly simple production, the outer envelope of the hose or tube is preferably not perforated. It can, however, also be perforated as long as the perforation holes in the outer envelope are not arranged congruently with the perforation holes in the inner envelope.

When reference is made in this description to a diffusion-inhibiting or diffusion-promoting effect of the components of the hose or tube, this preferably refers to hydrocarbons, in particular having a carbon number from 3 (i.e. propane and higher). Other gas molecules such as $H_2O$, $H_2S$ or $CO_2$ and $CH_4$ (methane) do not cause swelling of the diffusion layer and can pass through according to the "normal" principle of permeation (=sorption/desorption and diffusion) but at substantially lower diffusion currents than the swelling hydrocarbons. The materials of the inner envelope and the outer envelope are accordingly selected appropriately.

The inner envelope of the hose or tube preferably consists at least predominantly of polyvinyl chloride (PVC), polyvinylidene fluoride (PVDF) or polyethylene (PE), in particular high-density polyethylene (HDPE). Polyethylene-based materials are particularly preferred since they are easily workable, can be used in wide temperature ranges and can be sealed against adsorption by surface fluorination, as described above.

The outer envelope of the hose or tube preferably consists of ethylene vinyl acetate (EVA) and/or silicone. These materials form a diffusion layer in the sense described above, and are preferably airtight in the sense that they do not permit (macroscopic) convective air currents to pass through.

The advantages achieved by the invention are in particular that exploiting a swelling or curvature of the diffusion layer caused by the specimen gas concentration, in conjunction with sealing zones arranged locally in the region of the perforation holes, produces a sensor hose or sensor tube functioning as a "diffusion diode". This means that the property of permeability from the outside to the inside, which is essential for the function, is maintained, while the permeability is prevented in the opposite direction. It is thus possible to transport a gas specimen diffused into the hose or tube largely loss-free, i.e. with minimal transport damping, over large distances (typically 20 km to 50 km, i.e. approximately 10 times further than previously). The option of applying the sealing zones of the outer envelope and the sealing of the inner envelope at a later stage, by a simple method, increases the choice of available materials and possible construction principles. Typical uses of hoses or tubes of this type are in the field of leak monitoring in pipelines and tanks, in particular for crude oil and the refinery products thereof, such as petrol and diesel fuel.

Other features which are considered as characteristic for the invention are set forth in the appended claims.

Although the invention is illustrated and described herein as embodied in a hose or tube for transporting a gas specimen, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
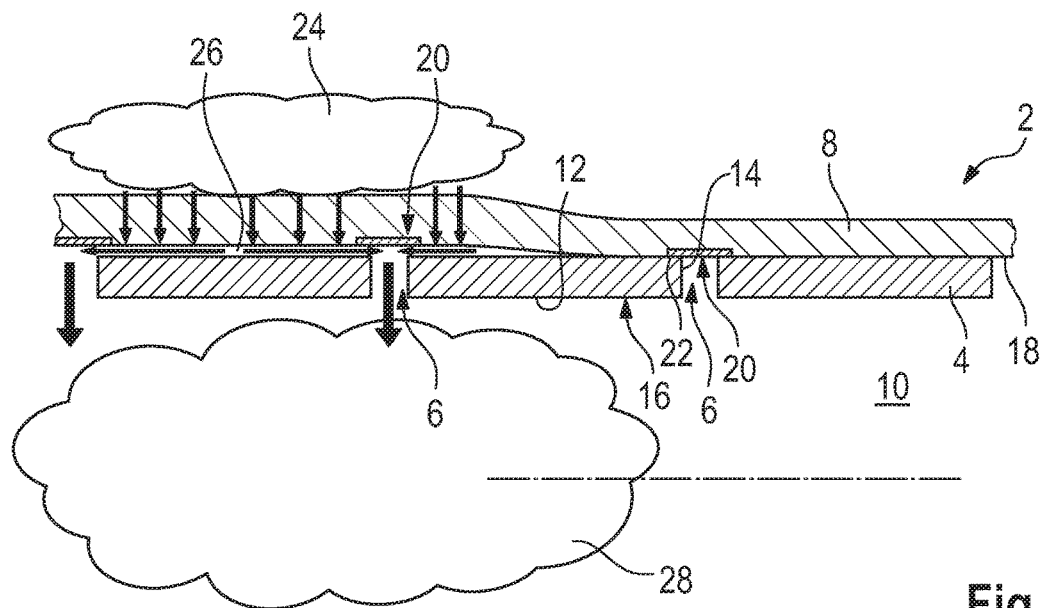
FIG. 1 is a diagrammatic, longitudinal sectional view through a sensor hose (just an upper half above a dashed axis of symmetry is shown) during a first operating state according to the invention.

Identical parts are provided with the same reference numerals in both figures.

Referring now to the figures of the drawings in detail and first, particularly to FIG. 1 thereof, there is shown a hose 2 shown in longitudinal section is acting as a sensor hose for receiving and transporting a gas specimen released into the surroundings, for example by leakage.

The hose 2 has a substantially hollow cylindrical inner envelope 4 made of high-density polyethylene (HDPE) which forms a diffusion barrier with regard to the gas components to be transported and detected, in particular hydrocarbons. The inner envelope 4 is provided with a perforation 6 in at least some longitudinal portions of the hose 2. Perforation holes 6 made in the inner envelope 4 are for example arranged in a regular pattern distributed around the periphery of the hose. For a hose envelope having an inner diameter of for example 10 mm, for example 800 perforation holes 6 having a diameter of for example 0.2 mm to 0.4 mm can be arranged inside a hose portion of 1 m in length.

A non-perforated hollow cylindrical outer envelope 8 made of ethylene vinyl acetate (EVA) is located around the inner envelope 4 and rests thereon in the normal state. Although the outer envelope 8 is airtight in the sense that it blocks high-volume convective airflows, it nevertheless forms a diffusion layer with regard to the above-mentioned gas components, and so permits the diffusion thereof.

Inner surfaces 12 of the inner envelope 4 which face an inside 10 of the hose and inner surfaces 14 of the inner envelope laterally defining the perforation holes 6 are coated with a sealing 16 generated for example by fluorination, which sealing increases the diffusion-inhibiting and adsorption-inhibiting effect of the inner envelope 4 compared with the basic material HDPE.

Furthermore, an inner surface 18 of the outer envelope 8 facing the inner envelope 4 is provided with sealing zones 20, generated by fluorination, in the region of the perforation holes 6 in the inner envelope 4 which are positioned beneath said inner surface, which sealing zones 20 slightly overlap the perforation holes 6 at the edges. This means that the respective sealing zone 20 extends laterally in an annular manner slightly beyond an edge 22 of the perforation hole 6. The size ratio of this overlapping annular surface to the (typically circular) cross-sectional area of the corresponding perforation hole 6, which ratio forms a measurement for the lateral overlap of the sealing zones 20 relative to the holes, is preferably in the range of between 0% (no overlap) and at most 50%. Apart from these small marginal regions, the sealing zones 20 are interrupted, i.e. not present, in the intermediate regions between the perforation holes 6. The sealing zones 20 thus essentially form covers for the outer opening of the perforation holes 6 facing the outer envelope 8.

When producing the hose 2, the sealing zones 20 and the sealing 16 can be generated in one work step by, in the case of a hose blank containing the inner envelope 4 and the outer envelope 8, injecting a fluorine-containing process gas at an overpressure compared with the surroundings into the inside 10 of the hose and leaving said gas for a while.

The effect of the described measures is are now described.

When, as shown in FIG. 1, specimen gas accumulates (shown here by a gas cloud 24) in a portion in the surroundings of the hose 2 due to a leak, the gas molecules diffusing into the outer envelope 8 result, at a sufficient concentration, in a swelling of the outer envelope 8. This results in the outer envelope 8 lifting slightly off the inner envelope 4 towards the outside in this region during the diffusion phase, and in the local formation of a radial gap or a short gap 26 between the outer envelope 8 and the inner envelope 4. In the process, the sealing zones 20 also lift off from the perforation holes 6 which they previously covered and sealed. Thus a flow path (shown by flow arrows in FIG. 1) for the gas molecules becomes available through the gap 26, past the sealing zones 20 and through the perforation holes 6 into the inside 10 of the hose. Consequently, the specimen gas accumulates in the inside 10 of the hose, as shown by the gas cloud 28.

Figure 2:
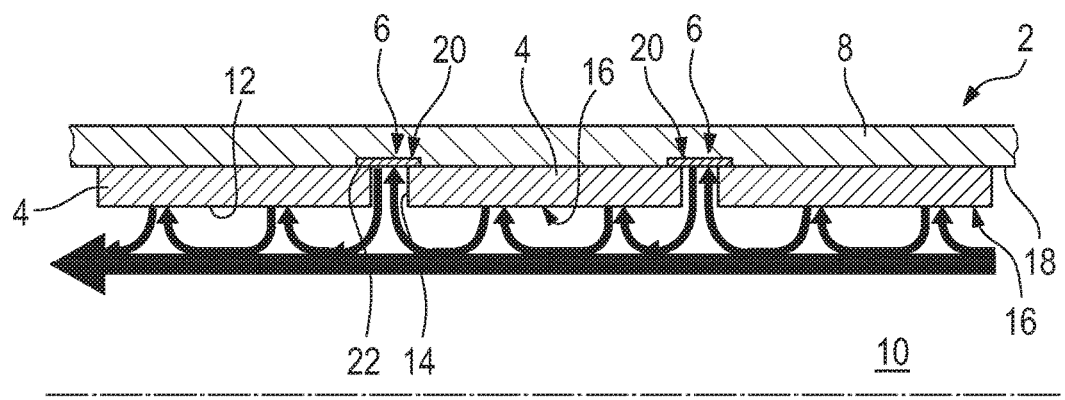
FIG. 2 is a longitudinal section through the sensor hose according to FIG. 1 during a second operating state.

The flow ratios during the subsequent transport phase are shown in FIG. 2. The specimen gas accumulated in the inside 10 of the hose is transferred in the hose 2, by a transport gas flow, for example air, to a detector or an analysis device arranged at some distance from the leak site. The outer envelope 8 fits closely to the inner envelope 4 in the length portions which contain negligible concentrations of the specimen gas outside the periphery of the hose. Consequently, the covers created by the sealing zones 20 also lie directly on the perforation holes 6 and seal the holes from leakage to the outside. This previously available flow path is therefore now sealed. In addition, the barrier effect of the inner envelope 4 is increased by the sealing 16 of the inner surfaces 12, 14. The specimen gas transported in the inside 10 of the hose thus cannot escape outside into the surroundings. Furthermore, the complete sealing 16 of the inner surfaces 12, 14 prevents gas molecules from sticking to the inner surfaces 12, 14.

The functionality of a diffusion diode, created in the described manner, ultimately permits unimpeded diffusion into the hose 2 of gas molecules to be detected and subsequently virtually loss-free transport (with only slight weakening of the concentration) over relatively long distances to an appropriate measuring device.

The following is a summary list of reference numerals and the corresponding structure used in the above description of the invention:

| 2 | hose |
| 4 | inner envelope |
| 6 | perforation hole |
| 8 | outer envelope |
| 10 | inside of the hose |
| 12 | inner surface of the inner envelope |
| 14 | inner surface of the perforation hole |
| 16 | sealing |
| 18 | inner surface of the outer envelope |
| 20 | sealing zone |
| 22 | edge |
| 24 | gas cloud |
| 26 | gap |
| 28 | gas cloud |

The invention claimed is:

1. A hose or tube for transporting a gas specimen, the hose or tube comprising:
an inner envelope forming a diffusion barrier and having a plurality of perforation holes formed therein; and
an outer envelope forming a diffusion layer and bearing against said inner envelope, said outer envelope having an inner surface with diffusion-inhibiting sealing zones overlapping said perforation holes of said inner envelope, each sealing zone of said sealing zones being disposed exclusively in a region of a respective one perforation hole of said perforation holes and not in intermediate regions between said perforation holes, said outer envelope configured to swell when gas molecules have diffused into said diffusion layer at a sufficient concentration, thereby lifting off said inner envelope, even in a region of said diffusion-inhibiting sealing zones.

2. The hose or tube according of claim 1, wherein said diffusion-inhibiting sealing zones together overlap all of said perforation holes.

3. The hose or tube according to claim 1, wherein the overlapping is chosen in such a manner that a ratio between a overlapped marginal area of said inner envelope and a cross-sectional area of a corresponding one of said perforation holes lies in a range of 0% to 50%.

4. The hose or tube according to claim 1, wherein a corresponding one of said diffusion-inhibiting sealing zones is formed by at least one of a chemical treatment or a physical treatment of a surface of said inner envelope in that area.

5. The hose or tube according to claim 4, wherein said diffusion-inhibiting sealing zones are generated through contact with a gas containing fluorine.

6. The hose or tube according to claim 1, further comprising a sealing, said inner envelope having an inner surface being substantially completely covered by said sealing.

7. The hose or tube according to claim 6, wherein said sealing is formed by at least one of a chemical treatment or a physical treatment of said inner surface of said inner envelope.

8. The hose or tube according to claim 7, wherein said sealing is generated through contact with a gas containing fluorine.

9. The hose or tube according to claim 8, wherein said outer envelope is not perforated.

10. The hose or tube according of claim 1, wherein at least one component of the hose or tube exhibits a diffusion-inhibiting or diffusion-promoting effect with regard to hydrocarbons.

11. The hose or tube according of claim 1, wherein said inner envelope is made of PVC or PE.

12. The hose or tube according of claim 1, wherein said outer envelope is made of EVA or silicone.

* * * * *